US008203708B2

(12) United States Patent
Lee et al.

(10) Patent No.: US 8,203,708 B2
(45) Date of Patent: Jun. 19, 2012

(54) SPECTRALLY ENCODED COHERENT ANT-STOKES RAMAN SCATTERING ENDOSCOPE (75) Inventors: Eun Seong Lee, Daejeon (KR); Jae Yong Lee, Cheongju-si (KR); Dae Won Moon, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 735 days.

(21) Appl. No.: 12/441,684

(22) PCT Filed: Nov. 27, 2008

(86) PCT No.: PCT/KR2008/006995
§ 371 (c)(1),
(2), (4) Date: Mar. 17, 2009

(87) PCT Pub. No.: WO2010/027125
PCT Pub. Date: Mar. 11, 2010

(65) Prior Publication Data
US 2010/0174145 A1    Jul. 8, 2010

(30) Foreign Application Priority Data
Sep. 5, 2008  (KR) ........................ 10-2008-0087778

(51) Int. Cl.
*G01J 3/44* (2006.01)
(52) U.S. Cl. ...................................................... 356/301
(58) Field of Classification Search .................. 356/301, 356/72–73; 600/182
See application file for complete search history.

(56) References Cited

U.S. PATENT DOCUMENTS

| 4,922,495 A * | 5/1990 | Bobbs et al. ...................... 372/3 |
| 6,370,406 B1 | 4/2002 | Wach et al. |
| 2007/0088219 A1 | 4/2007 | Xie et al. |
| 2008/0117416 A1 | 5/2008 | Hunter et al. |

* cited by examiner

*Primary Examiner* — Tarifur Chowdhury
*Assistant Examiner* — Abdullahi Nur
(74) *Attorney, Agent, or Firm* — Kile Park Goekjian Reed & McManus PLLC (57) ABSTRACT Disclosed is a spectrally encoded coherent anti-Stokes Raman scattering (CARS) endoscope that is capable of spatially encoding spectral dispersions of two light sources having frequency difference as much as a Raman shift and overlapping two laser beams on a position where a sample to be measured is placed, thereby acquiring a spatial distribution of CARS signals.

7 Claims, 4 Drawing Sheets

SPECTRALLY ENCODED COHERENT ANT-STOKES RAMAN SCATTERING ENDOSCOPE

BACKGROUND OF THE INVENTION

1. Field of the Invention

The present invention relates to a spectrally encoded coherent anti-Stokes Raman scattering (CARS) endoscope that is capable of spatially encoding spectral dispersions of two light sources having frequency difference as much as a Raman shift and overlapping two laser beams on a position where a sample to be measured is placed, thereby acquiring a spatial distribution of CARS signals.

2. Description of the Related Art

A visual observation on morphological or physiological change of diseased tissue is an important process required in early diagnosis of diseases. In particular, the wide clinical use of a laparoscope or an endoscope enabling direct observation in vivo greatly reduces lethality of patients and considerably reduces costs required for disease diagnoses. The endoscope has an advantage in that the endoscope is capable of observing an object without incision or in a minimally invasive condition in a biological research as well as in a medical research. As a result, the endoscope has been developed in various forms. Because it is characteristically required for the endoscope to be introduced into a living body to acquire an image, it is required for an endoscope probe to be as small and thin as possible, and it is also required for several optical components constituting an imaging optical system to be installed at the head part of the endoscope probe while being successfully integrated in a very small space. In most cases, a bundle of optical fibers well combed are used to guide an image acquired in vivo to the outside. However, a considerably great number of optical fibers are needed to acquire a fine image. As a result, the thickness of the endoscope probe increases as a whole. In this case, the endoscope is not appropriate for observing the inner wall of a blood vessel or internal tissue of small animals. In another approach, a micro optical mirror is installed at the head part of the endoscope probe, a laser beam introduced from the outside through a single mode optical fiber is scanned on a sample, a series of scattered light signals generated are guided to the outside through the optical fiber, and the guided light signals are processed at the outside to reproduce an image. This approach has an advantage of reducing the thickness of the endoscope probe; however, this approach encounters a fairly difficult, challengeable problem in that it is required to manufacture and integrate a high-speed scanning apparatus in a small space.

SUMMARY OF THE INVENTION

Therefore, the present invention has been made in view of the above problems, and it is an object of the present invention to provide a spectrally encoded coherent anti-Stokes Raman scattering (CARS) endoscope in which the interior of the endoscope is miniaturized by using a simple diffraction optical device for dispersing light instead of using a complicated apparatus for scanning a laser beam on a sample at high speed.

In accordance with the present invention, the above and other objects can be accomplished by the provision of a spectrally encoded CARS endoscope, including: a cylindrical main body; a Stokes beam optical fiber and a pump beam optical fiber installed at one side of the main body for transmitting a Stokes beam, having an arbitrary frequency band, generated from a Stokes light source and a pump beam, generated from a pump light source, making medium molecules of a sample excited together with the Stokes beam, respectively, the Stokes beam optical fiber and the pump beam optical fiber being disposed above and below, respectively, such that the Stokes beam optical fiber and the pump beam optical fiber are spaced apart from each other by a predetermined distance, to change incident angles of the Stokes beam and the pump beam; a collimator lens installed in the main body at rears of the optical fibers for collimating the Stokes beam and the pump beam transmitted from the respective optical fibers; a diffraction grating installed in the main body at the rear of the collimator lens for diffracting the collimated Stokes beam and the collimated pump beam such that the collimated Stokes beam and the collimated pump beam have the same spectral dispersion; a reflection mirror installed in the main body for transmitting the reflected Stokes beam and the reflected pump beam, the reflection mirror comprising a dichroic reflection part for transmitting the diffracted pump beam, reflecting the diffracted Stokes beam, and re-reflecting CARS beams generated from the sample to the diffraction grating and a full reflection part for fully reflecting the pump beam transmitted through the dichroic reflection part; an objective lens installed in the main body at the other side of the main body for condensing the pump beam and the Stokes beam reflected from the reflection mirror to the sample; and a CARS beam transmission part for transmitting the CARS beams to a spectroscope.

The CARS beam transmission part may be located at one side of the main body where the optical fibers are installed.

The dichroic reflection part and the full reflection part of the reflection mirror may be implemented by a dichroic reflection mirror and a full reflection mirror, respectively, and the spectrally encoded CARS endoscope may further include an angle adjustment device for adjusting an angle defined between the dichroic reflection mirror and the full reflection mirror.

The angle adjustment device may include a support part disposed between the dichroic reflection mirror and the full reflection mirror for supporting the dichroic reflection mirror and adjusting an inclination angle of the dichroic reflection mirror through a movement thereof and a distance adjustment screw coupled to the main body, while the distance adjustment screw is in contact with the support part, for adjusting the movement distance of the support part.

The dichroic reflection part and the full reflection part of the reflection mirror may be implemented by a dichroic reflection coating and a full reflection coating formed at one major surface and the other major surface of the reflection mirror, respectively, and the reflection mirror may be installed such that the reflection mirror is inclined at a predetermined angle to an incident pump beam and an incident Stokes beam.

The angle of the reflection mirror may be decided by the following equation.

$$\alpha = (\theta_{pd} - \theta_{sd})/2n$$

Where, $\alpha$ is an angle of the reflection mirror, $(\theta_{pd} - \theta_{sd})$ is a diffraction angle difference between the pump beam and the Stokes beam, and n is a refractive index of the reflection mirror.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Now, a spectrally encoded coherent anti-Stokes Raman scattering (CARS) endoscope according to an embodiment of the present invention will be described in detail with reference to the accompanying drawings.

According to an embodiment of the present invention, there is provided a spectrally encoded endoscope that is capable of achieving coincidence between spectral dispersions of a pump beam and a Stokes beam by using a simple diffraction optical device for dispersing light instead of using a complicated apparatus for scanning a laser beam on a sample at high speed, thereby accomplishing the same effect as the high-speed scanning using such a simple miniaturized apparatus. The spectrally encoded endoscope is based on a concept of a wavelength division multiplexing method. In the spectrally encoded endoscope, a wideband laser beam is transmitted to the head part of the endoscope through a single mode optical fiber, the laser beam is spatially dispersed by a diffraction grating, optical signals generated when respective wavelength components of the laser beam scattered from the sample are guided to the outside through the optical fiber, and the guided optical signals are spectrally dispersed by a spectroscope, thereby reproducing a spatial signal distribution generated from the sample as a spectral signal distribution. That is, spatial encoding of the spectral dispersion is carried out at an axis requiring high-speed scanning, of two scanning axes of a micro mirror for two-dimensional imaging, using the diffraction grating, instead of spatial scanning. At the present time, this technology is restrictively applied to reflectivity distribution imaging due to the difference of a refractive index or absorptivity, which is a linear optical characteristic of the sample; however, it is easily expected that the technology concerned may be applicable to imaging on a nonlinear optical characteristic of the sample.

Figure 1:
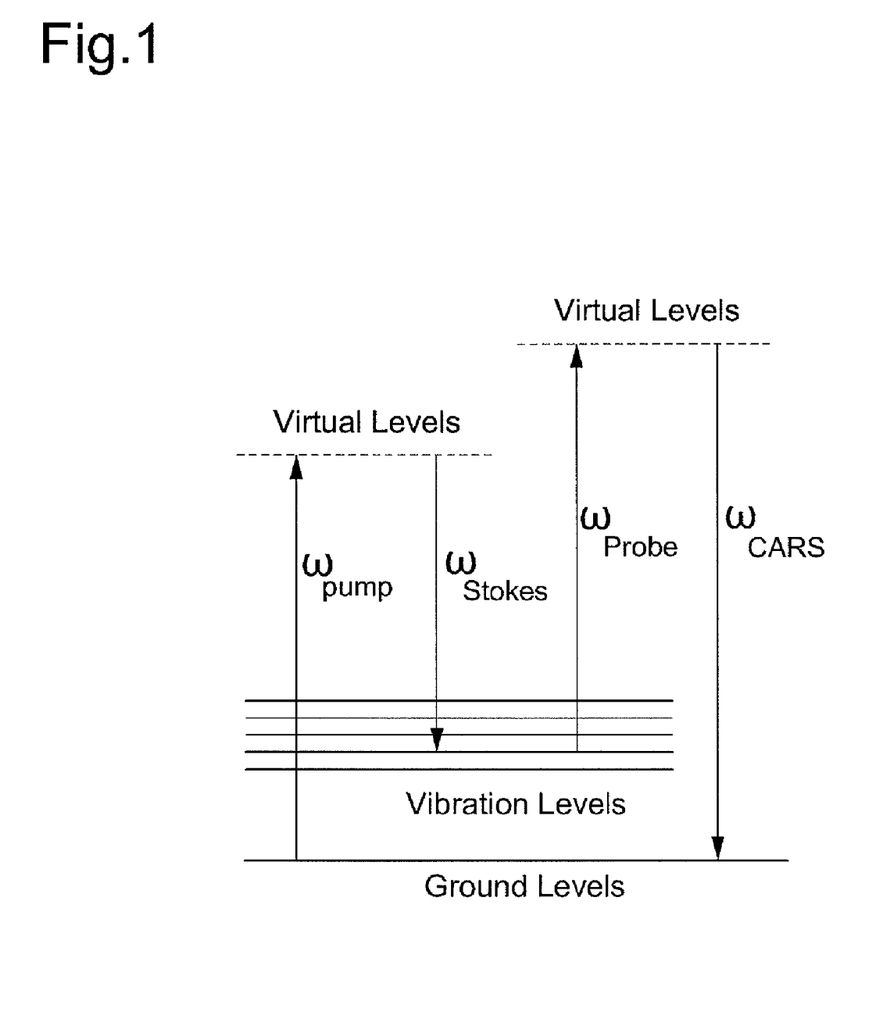
FIG. 1 is an energy diagram illustrating a coherent anti-Stokes Raman scattering (CARS) phenomenon.

The coherent anti-Stokes Raman scattering (CARS) exhibits a molecular vibration resonance property. Therefore, the CARS has an advantage of providing spectral information of the sample. When the CARS is applied to a microscope image system, it is possible to acquire a spatial distribution of chemical compositions of the sample as an image. By virtue of a coherent characteristic of a signal beam, it is possible for the CARS to provide signal intensity much greater than conventional Raman microscope imaging, and it is possible for the CARS to perform label-free three-dimensional imaging without a sample dyeing process unlike a confocal fluorescence microscope. As a result, the CARS has been developed as a strong imaging tool in a bio-medical field. As shown in an energy diagram of FIG. 1, the CARS is a third order nonlinear optical phenomenon in which two laser beams having different wavelengths, i.e., a pump beam and a Stokes beam, are irradiated to a sample to excite a molecular vibration mode resonant with their beat frequency, and a probe beam is anti-Stokes Raman scattered. At this time, the probe beam and the pump beam use identical lasers having the same wavelength, and therefore, the frequency of a signal beam is represented by $2\nu_{pump}-\nu_{stokes}$. Because of a signal generation characteristic of the CARS, therefore, the spectrally encoded CARS endoscope optical system needs a unique design concept in which it is required to simultaneously consider spectral dispersions at two different wavelength bands unlike a conventional spectrally encoded endoscope.

The most important kernel condition to be considered in the first place to embody a spectrally encoded CARS endoscope is that the spectral dispersions of a pump beam and a Stokes beam to be irradiated to the top of a sample and dispersed by a diffraction grating must have the same value. That is, the following equation must be satisfied.

$$\left(\frac{d\theta}{d\tilde{\nu}}\right)_{Pump} = \left(\frac{d\theta}{d\tilde{\nu}}\right)_{Stokes} \quad (1)$$

Figure 2:
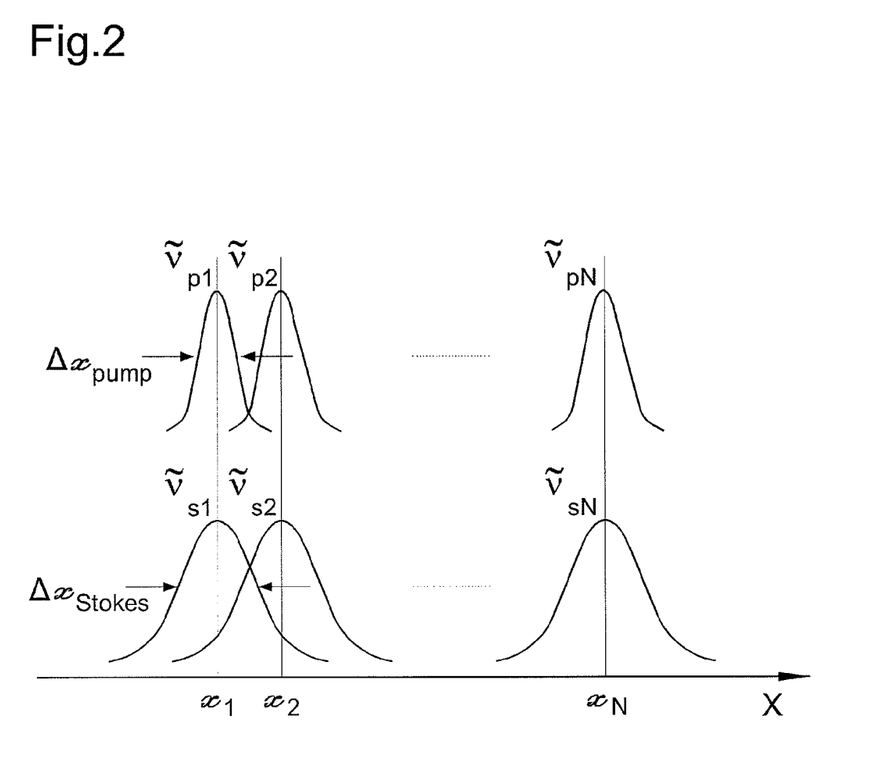
FIG. 2 is a view illustrating a spatial encoding condition of spectral dispersions to materialize spectrally encoded coherent anti-Stokes Raman scattering (SE-CARS)

Where, $\tilde{\nu}$ indicates wavenumber, and $\theta$ indicates a diffraction angle. This is a condition to uniformly maintain the wavenumber difference between the two beams, i.e., a Raman shift value, at an imaging area. Second, it is required for spectra of the two laser beams to be spatially overlapped at the same position of the sample surface. As a result, only molecular vibration modes of a specific Raman shift on the sample surface are activated to acquire a distribution of CARS signals. FIG. 2 schematically illustrates these two conditions. When a laser beam assumed as Gaussian is incident upon the diffraction grating, is spectrally dispersed by the diffraction grating, and is condensed on the sample surface by a condenser lens, respective wavenumber components $\tilde{\nu}_i$ have a Gaussian light intensity distribution of a line width $\Delta x$ at respective positions of the X axis. $\Delta x$ is an amount having a close relation with spatial resolution of an image. $\Delta x$ is represented by $0.61\lambda/NA$. NA is a numerical aperture of the condenser lens, and $\lambda$ is a wavelength. The upper part of the FIG. 2 shows a distribution of the pump beam, and the lower part of the FIG. 2 shows a distribution of the Stokes beam at the same X axis. When the Stokes beam and the pump beam satisfy Equation (1) to embody the spectrally encoded CARS imaging, Equation (2) is realized to acquire CARS signals having different wavenumbers represented by Equation (3) at the respective positions. That is, spectrally encoded signals having the same Raman shift and different wavenumbers of the CARS signals at the respective positions.

$$\tilde{\nu}_{p1}-\tilde{\nu}_{s1} = \tilde{\nu}_{p2}-\tilde{\nu}_{s2} = \ldots = \tilde{\nu}_{pN}-\tilde{\nu}_{sN} \quad (2)$$

$$2\tilde{\nu}_{p1}-\tilde{\nu}_{s1}, 2\tilde{\nu}_{p2}-\tilde{\nu}_{s2}, \ldots, 2\tilde{\nu}_{pN}-\tilde{\nu}_{sN} \quad (3)$$

At this time, it is possible to adjust a Raman shift value by relatively moving the spectrum of one laser beam with respect to the other laser beam. In the above, it is assumed that the overall bandwidth $\Delta\tilde{\nu}_L$ of each laser is sufficient small as compared with the wavelength $\tilde{\nu}_L$ of the laser, and therefore, the dependency of the diffraction angle on the wavenumber is linear-functional within the bandwidth. Most of the generated CARS signals advance frontward. However, a respectable number of the signals are reflected rearward in living tissue exhibiting a high scattering property, are guided to the outside by the condenser lens, and are resolved by the spectroscope, thereby acquiring a spatial distribution of the spectrally encoded CARS signals.

The CARS signals are generated at a place where the two laser beams are overlapped with each other, and therefore, a field of view (FOV) is decided by a laser having a smaller bandwidth. When Calculating, the field of view based on the bandwidth $\tilde{V}_L$ of a given incident laser is represented by $FOV = f\Delta\Theta_{FOV} = f(d\Theta/d\tilde{V})\Delta\tilde{V}_L$. Where, f is a focal distance of a objective lens. In conclusion, it is required to enlarge spectral dispersion ($d\Theta/d\tilde{V}$) as much as possible to enlarge the field of view at the given laser bandwidth. When exceeding a limit, however, laser energy spreads out over a wide range, and therefore, the power density of the laser applied to the sample surface decreases, with the result that it is difficult to generate a sufficient number of signals. Consequently, this aspect must be also included in important considerations when designing the spectrally encoded CARS endoscope. Finally, a one-dimensional image acquired by the spectral encoding is linked to a low-speed Y-axis scanning apparatus, which is driven mechanically, to form a two-dimensional image.

In this embodiment, the optical system installed at the head part of the endoscope probe is designed such that a laser beam guided by a single mode optical fiber is collimated by a gradient-index (GRIN) lens, is dispersed by a transmission type diffraction grating, and is condensed on the sample surface by another GRIN lens. Ray tracing is based on a first order geometrical optics. Analysis and correction of high-degree monochromatic aberration and chromatic aberration through high-degree geometrical optic ray tracing are out of the question, which, therefore, are not considered herein.

As previously described, the kernel in designing the spectrally encoded CARS endoscope is to achieve coincidence between spectral dispersions of the pump beam and the Stokes beam using a single diffraction grating. In order to find this condition, a basic relation of the diffraction grating may be expressed as a function of wavenumber represented by Equation (4).

$$m\frac{1}{\tilde{v}} = a(\sin\theta_i + \sin\theta_d) \quad (4)$$

A given wavenumber $\tilde{V}$ and a grating line gap a show a relationship between an incident angle $\theta_i$ and an m-th diffraction angle $\theta_d$. In this embodiment, limitation is given to a first diffraction (m=1). From the above relation, a spectral dispersion is represented by Equation (5). Since the spectral dispersions at wavenumber bands of the pump beam and the Stokes beam are to be the same, a relation represented by Equation (6) is derived.

$$\frac{\Delta\theta_d}{\Delta\tilde{v}} = \frac{1}{\tilde{v}^2 a \cos\theta_d} \quad (m=1) \quad (5)$$

$$\frac{\cos\theta_{sd}}{\cos\theta_{pd}} = \frac{\tilde{v}_p^2}{\tilde{v}_s^2} \quad (6)$$

Where, $\theta_{pd}$, $\theta_{sd}$ are diffraction angles of the pump beam and the Stokes beam, respectively. Now, if it is possible to find a diffraction condition simultaneously satisfying the three equations, i.e., Equation (4) to Equation (6), from two different wavenumber bands, the spectrally encoded CARS imaging may be embodied. According to Equation (6), two diffraction angles must differ from each other. Consequently, the simplest condition considerable in the first place is that the incident angles of the pump beam and the Stokes beam are the same, i.e., two incident laser beams are guided from a single optical fiber, are collimated, and are incident upon the diffraction grating. In this condition, Equation (7) is derived from the three relations represented by Equation (4) to Equation (6). However, the left side and the right side of this equation have different signs, and therefore, a physical condition to realize an equality does not exist. Consequently, this condition is excluded from a design possibility.

$$\sqrt{1 - \cos^2\theta_{pd}} - \sqrt{1 - \left(\frac{\tilde{v}_p}{\tilde{v}_s}\right)^4 \cos^2\theta_{pd}} = \frac{c(\tilde{v}_s - \tilde{v}_p)}{a\tilde{v}_s\tilde{v}_p} \quad (7)$$

Figure 3:
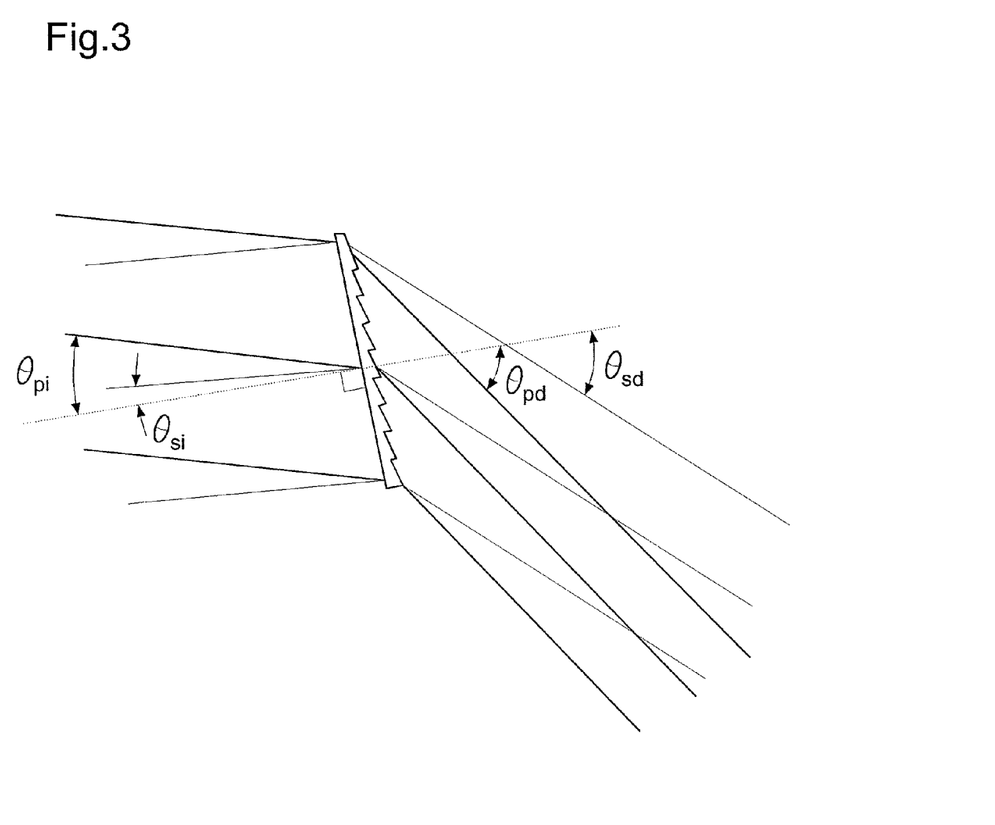
FIG. 3 is a view illustrating a geometrical position relationship between a Stokes beam and a pump beam to be formed by a diffraction grating to achieve coincidence between pump and stokes spectral dispersions.

In conclusion, it is presumed that the pump beam and the Stokes beam must have different incident angles as shown in FIG. 3. What this situation implies is that, when both the pump beam and the Stokes beam are guided using only a single optical fiber, it is not possible to achieve coincidence between the spectral dispersions of the pump beam and the Stokes beam at the two wavenumber bands. That is, the two laser beams need their respective optical fibers. This rather provides an advantageous aspect in operating the apparatus. It is because it is possible to eliminate cross talk between two high-power laser beams in a single optical fiber. As will be described below, it is possible to compensate for chromatic aberration caused by a collimator lens and an objective lens due to the use of the respective optical fibers by adjusting the positions of the respective optical fibers. In FIG. 3, $\theta_{pi}$, $\theta_{si}$ are incident angles of the pump beam and the Stokes beam, respectively. When Equation (4) to Equation (6) are satisfied by adjusting a total of four angles, i.e., the incident angles and the diffraction angles of the respective laser beams, the same dispersion condition is achieved. Since the number of the equations is 3, and the number of variables is 4, various conditions may be possible. However, when the diffraction angle is too large, anamorphic distortion of the diffracted beam is excessive. On the other hand, when the diffraction angle is too small, dispersion is also small. In this embodiment, therefore, the diffraction angle of the Stokes beam is arbitrarily set to 65 degrees ($\theta_{sd}$=65 degrees), and the other angles are decided accordingly, in consideration of the convenience in design. These are values that can be directly calculated when the grating line interval a of the diffraction grating and the wavenumber of the incident laser are set.

It is advantageous to use an incident laser having a wide bandwidth to provide a wide field of view in spectrally encoded imaging. However, the bandwidth of an ultra short pulse laser, which is already on the market, is very limited. In this embodiment, two mode-lock titanium sapphire lasers of a 54 femto second pulse width having center wavelengths at 740 nm (13514 cm$^{-1}$) and 938 nm (10664 cm$^{-1}$) are set to be the pump beam and the Stokes beam, respectively, in consideration of such limitation and a CARS imaging wavelength region applied the most frequently. When it is assumed that laser pulses are within a Fourier transform limit, the laser pulses have a bandwidth of 274 cm$^{-1}$ or wavelengths of 15 nm and 24.1 nm. The wavenumber difference corresponding to the difference between the two wavelengths is the region coinciding with the Raman vibration number of lipid molecules in living tissue, which is included in a Raman shift band on which research using the CARS is being the most actively carried out. In order to acquire a sufficient field of view within the limited laser bandwidth, it is required to enhance spectral dispersion by the diffraction grating. As previously described, however, excessively high dispersion reduces the power of an incident laser irradiated to the sample per unit area. In this embodiment, therefore, the spectral width within the spatial width $\Delta x_{pump}$ of the pump beam of FIG. 2 is set to be 7.4 cm$^{-1}$ ($\Delta\tilde{V}_{pump}$=7.4 cm$^{-1}$, $\Delta\lambda$=0.4 nm). This value is approximate to a Raman line width of a living molecule and a laser bandwidth having been already used in pico second narrow band CARS imaging. Therefore, this value is an actual value. Since the spectral width is eventually connected with the spectral resolution of the diffraction grating by $\tilde{V}/\Delta\tilde{V}=N$, the number N of grating lines is decided from the given wavenumber $\tilde{V}$ of the pump beam. At the set pump wavelength of 740 nm, this value is approximately 13514/7.4 to 1800, and the number of resolvable image pixels are approximately 274 cm$^{-1}$/7.4 cm$^{-1}$=37. However, this number of pixels is possible only when using a perfect objective lens that is capable of forming a diffraction limit focus without aberration. For an actual lens, therefore, the number of pixels is relatively small. When the diameter of the endoscope probe pursued in this embodiment is set to be approximately 2.5 mm or less, and a diffraction grating having a diameter of 2 mm is used, the grating line density is 900 grooves/mm, and the grating line interval is 1.11 μm (a=1.11 μm). When calculating the incident angles and the diffraction angles of the pump beam and the Stokes beam based on the decided wavenumber of the incident laser and the standards of the diffraction grating, $\theta_{pi}$=17.38 degrees, $\theta_{si}$=3.56 degrees, $\theta_{pd}$=74.75 degrees, and $\theta_{sd}$=65 degrees. When calculating the spectral dispersion and the field of view from the diffraction angle, 74.75 degrees, of the pump beam using Equation (5), the spectral dispersion is 0.000185 radian/cm$^{-1}$, and the field of view $\Delta\theta_{FOV}$=0.051 radian.

The overall construction of the endoscope is completed by installing a collimator lens for collimating incident laser beams guided from the optical fibers at the left side of FIG. 3 and an objective lens for condensing diffracted beams at the right side of FIG. 3. The endoscope optical system designed as described above is illustrated in FIG. 4.

Figure 4:
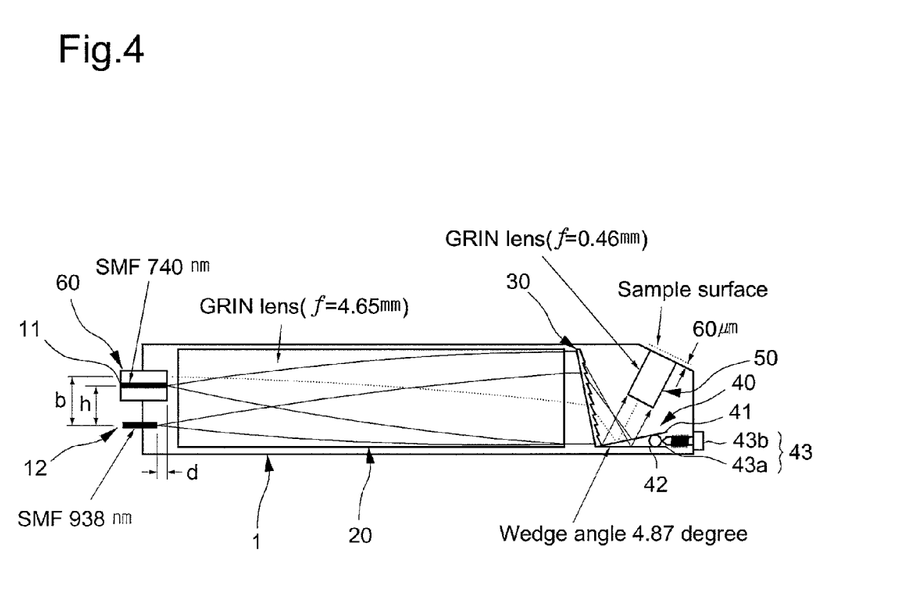
FIG. 4 is a view illustrating the structure of an SE-CARS endoscope according to an embodiment of the present invention.

As shown in FIG. 4, the spectrally encoded coherent anti-Stokes Raman scattering endoscope includes a cylindrical main body 1, a Stokes beam optical fiber 11 and a pump beam optical fiber 12 disposed above and below, respectively, such that the Stokes beam optical fiber 11 and the pump beam optical fiber are spaced apart from each other by a predetermined distance, for transmitting a Stokes beam and a pump beam, respectively, a collimator lens 20 for collimating the Stokes beam and the pump beam transmitted from the respective optical fibers 11 and 12, a diffraction grating 30 for diffracting the collimated Stokes beam and the collimated pump beam such that the Stokes beam and the pump beam have the same spectral dispersion, a reflection mirror 40, including a dichroic reflection part for reflecting the Stokes beam and re-reflecting CARS beams generated from a sample to the diffraction grating 30 and a full reflection part for fully reflecting the pump beam, for transmitting the reflected Stokes beam and the reflected pump beam, an objective lens 50 for condensing the reflected pump beam and the reflected Stokes beam to the sample, and a CARS beam transmission part 60 for transmitting the CARS beams to a spectroscope.

The Stokes beam optical fiber 11 and the pump beam optical fiber 12 are installed at one side of the main body 1. The Stokes beam optical fiber 11 and the pump beam optical fiber 12 are disposed above and below, respectively, such that the Stokes beam optical fiber 11 and the pump beam optical fiber 12 are spaced apart from each other by the predetermined distance. The Stokes beam optical fiber 11 and the pump beam optical fiber 12 transmit a Stokes beam having an arbitrary frequency band generated from a Stokes light source and a pump beam making medium molecules of the sample unstable together with the Stokes beam, respectively.

The collimator lens 20 is installed in the main body 1 at the rears of the optical fibers 11 and 12. The collimator lens 20 serves to collimate the Stokes beam and the pump beam transmitted from the respective optical fibers 11 and 12.

The diffraction grating 30 is installed in the main body 1 at the rear of the collimator lens 20. The diffraction grating 30 serves to diffract the collimated Stokes beam and the collimated pump beam such that the collimated Stokes beam and the collimated pump beam have the same spectral dispersion.

The reflection mirror 40 is installed in the main body 1 for transmitting the reflected Stokes beam and the reflected pump beam. Specifically, the reflection mirror 40 includes a dichroic reflection part for transmitting the diffracted pump beam, reflecting the diffracted Stokes beam, and re-reflecting CARS beams generated from the sample to the diffraction grating 30 and a full reflection part for fully reflecting the pump beam transmitted through the dichroic reflection part.

The objective lens 50 is installed in the main body 1 at the other side of the main body 1. The objective lens 50 serves to condense the pump beam and the Stokes beam reflected from the reflection mirror 40 to the sample.

The CARS beam transmission part 60 is located at one side of the main body where the optical fibers 11 and 12 are installed. The CARS beam transmission part 60 serves to transmit the CARS beams to a spectroscope (not shown).

Generally, lenses for the endoscope are implemented by GRIN lenses that can be miniaturized. In this embodiment, a lens having a focal distance of 4.65 mm (GT-LFRL-180-024-20-cc, a diameter of 2 mm, a length of 10.68 mm, NA of 0.19), manufactured by GRINTECH and already on the market, is used as the collimator lens 20, and a lens having a focal distance of 0.46 mm (GT-LFRL-180-024-20-cc, a diameter of 0.5 mm, a length of 1.06 mm, NA of 0.52), also manufactured by GRINTECH and already on the market, is used as the objective lens 50. These lenses are known to exhibit relatively small chromatic aberration at a wavelength area of an incident laser and to provide a focal spot size approximate to the diffraction limit in condensing collimated beams. The incident angle difference $\theta_{pi}$-$\theta_{si}$ between the two laser beams incident upon the diffraction grating is 13.82 degrees (=0.241 radian). Consequently, when the collimation is performed using the GRIN lens having a focal distance of 4.65 mm, the distance between the two optical fibers is set to be 1.12 mm (h=1.12 mm). The focal distance of the GRIN lens to be used as the objective lens is 0.46 mm, and therefore, the field of view is 23.5 μm (0.46×0.051 radian=23.5 μm). However, as shown in FIG. 3, the diffraction angles of the pump beam and the Stokes beam are different from each other (in this case, by 9.75 degrees). For this reason, when the pump beam and the Stokes beam are condensed by the objective lens in such a state, the two beams are not overlapped with each other on the same position of the sample surface.

In order to simply solve this problem, a dichroic reflection mirror and a full reflection mirror, combined in the form of a wedge, may be installed in front of the objective lens, as shown in FIG. 4. In this case, the dichroic reflection part and the full reflection part of the reflection mirror 40 are implemented by the dichroic reflection mirror and the full reflection mirror, respectively, and an angle adjustment device 43 is provided to adjust the angle between the dichroic reflection mirror 41 and the full reflection mirror 42. The angle adjustment device 43 includes a support part 43a disposed between the dichroic reflection mirror 41 and the full reflection mirror 42 for supporting the dichroic reflection mirror 41 and adjusting the inclination angle of the dichroic reflection mirror 41 through the movement thereof and a distance adjustment screw 43b coupled to the main body 1, while the distance adjustment screw 43b is in contact with the support part 43a, for adjusting the movement distance of the support part 43a.

The mirror located below the support part 43a is the full reflection mirror for reflecting a pump beam, and the mirror located above the support part 43a while being inclined at an angle of 4.87 degrees is the dichroic reflection mirror for transmitting a pump beam and reflecting a Stokes beam and generated CARS beams. A single glass wedge may be used instead of the two mirrors. To this end, the dichroic reflection part and the full reflection part of the reflection mirror 40 are implemented by a dichroic reflection coating and a full reflection coating formed at one major surface and the other major surface of the reflection mirror 40, respectively. The reflection mirror is installed such that the reflection mirror is inclined at a predetermined angle to an incident pump beam and an incident Stokes beam. At this time, the full reflection coating is formed at one major surface of the reflection mirror 40, and the dichroic reflection coating is formed at the other major surface of the reflection mirror 40, to obtain a wedge angle of 9.75/2n (n is a refractive index of glass). If possible, crown glass exhibiting small dispersion is used to minimize the effect with respect to the total spectral dispersion such that Equation (1) is maintained. When fused silica (Abbe number 67.8) is used as the glass wedge, the effect is approximately $\frac{1}{1000}$, which is negligible.

As previously described, the two GRIN lenses have longitudinal chromatic aberration in which the focal distance to the Stokes beam is slightly longer than the focal distance to the pump beam. The focal distance difference due to the chromatic aberration at the respective wavelength bands (740 nm, 938 nm) is approximately 30 μm for the collimator lens and approximately 5 μm for the objective lens. Consequently, when the relative position difference between the two optical fibers in the longitudinal direction is adjusted, such that d=0.53 mm, in the vicinity of a nominal focus of the collimator lens, it is possible to achieve coincidence between condensed points of the two incident laser beams, thereby compensating for the longitudinal chromatic aberration.

In the above, the optical system for achieving coincidence between the spectral dispersions of the pump beam and the Stokes beam on the sample surface to generate spectrally encoded CARS signals from a specific Raman shift (2850 $cm^{-1}$) was described. Hereinafter, a method of re-reflecting some of the generated CARS signals and guiding the re-reflected CARS signals to the outside through the objective lens, the diffraction grating, and another optical fiber, i.e., the CARS beam transmission part 60 will be described. Since the incident angle of the central CARS signal beam incident upon the diffraction grating is equal to the diffraction angle of the Stokes beam, the incident angle of the CARS signal beams is 65 degrees. The diffraction angle of the CARS signal beams diffracted to the collimator lens through the diffraction grating is 20.87 degrees. As shown in FIG. 4, therefore, the CARS signal beams are condensed at a place distant, by b=1.4 mm, from the Stokes beam optical fiber by the collimator lens. However, the spectral dispersion of the spectrally encoded CARS signals generated over a wavelength of 606 nm to a wavelength of 616.2 nm about a wavelength of 611 nm is not equal to the spectral dispersion of the pump beam or the Stokes beam. For this reason, the signal beams are not diffracted at a single angle of 20.87 degrees but are distributed within a range of approximately 0.75 degrees. As a result, the signal beams are not condensed to a point but spread out with a size of 60 μm. Furthermore, most of the CARS signals reaching the optical fiber are beams scattered and re-reflected from the sample, with the result that it is not possible for the CARS signals to be condensed to a small point. Consequently, it is effective for the CARS beam transmission part 60 to use a multi mode optical fiber instead of a single mode optical fiber. Alternatively, it may be effective to manufacture a pump beam optical fiber having a cladding of a sufficiently large diameter such that the guide is carried out in a cladding mode.

As described above, the present invention is equally applicable to the overall range of a Raman shift of living molecules. Consequently, when appropriately calculating design numerical values such that the design numerical values are suitable for Raman shifts of the respective molecular vibration modes, it is possible to complete the design of an endoscope in several vibration modes. The design numerical values of the spectrally encoded CARS (SE-CARS) endoscope in the previously calculated CH2 molecular vibration mode and in an amide coupling mode (1649 $cm^{-1}$) within a molecular vibration finger print region obtained by the same method are given as indicated in Table 1.

TABLE 1

Design numerical values of SE-CARS endoscope optical system calculated at two different Raman shifts (laser bandwidth: 274 $cm^{-1}$, transmission type diffraction grating: 900 grooves/mm, diameter: 2 mm)

| | | |
|---|---|---|
| Raman shift ($cm^{-1}$) | 2350 | 1649 |
| Pump beam wavenumber ($cm^{-1}$) | 13514 | 13514 |
| Stokes beam wavenumber ($cm^{-1}$) | 10664 | 11865 |
| CARS signal wavenumber ($cm^{-1}$) | 16364 | 15163 |
| Incident angle of pump beam (degree) | 17.38 | 17.38 |
| Diffraction angle of pump beam (degree) | 74.75 | 74.75 |
| Incident angle of Stokes beam (degree) | 3.56 | 10.45 |
| Diffraction angle of Stokes beam (degree) | 65 | 70.05 |
| Field of view (μm) | 23.5 | 23.5 |
| b (mm) | 1.4 | 0.79 |
| h (mm) | 1.12 | 0.56 |
| d (mm) | 0.53 | 0.21 |
| Wedge angle of dichroic reflection mirror (degree) | 4.87 | 2.35 |

Although the exemplary embodiment of the present invention has been disclosed for illustrative purposes, those skilled in the art will appreciate that various modifications, additions and substitutions are possible, without departing from the scope and spirit of the invention as disclosed in the accompanying claims.

As is apparent from the above description, the present invention has an advantage of not only utilizing an advantage of CARS spectral analysis exhibiting a molecular vibration resonance property but also achieving coincidence. between spectral dispersions of a pump beam and a Stokes beam by using a simple diffraction optical device for dispersing light instead of using a complicated apparatus for scanning a laser beam on a sample at high speed, thereby accomplishing the same effect as the high-speed scanning using such a simple miniaturized apparatus.

What is claimed is:

1. A spectrally encoded coherent anti-Stokes Raman scattering (CARS) endoscope, comprising:
    a cylindrical main body;
    a Stokes beam optical fiber and a pump beam optical fiber installed at one side of the main body for transmitting a Stokes beam, having an arbitrary frequency band, generated from a Stokes light source and a pump beam, generated from a pump light source, making medium molecules of a sample excited together with the Stokes beam, respectively, the Stokes beam optical fiber and the pump beam optical fiber being disposed above and below, respectively, such that the Stokes beam optical fiber and the pump beam optical fiber are spaced apart from each other by a predetermined distance, to change incident angles of the Stokes beam and the pump beam;

a collimator lens installed in the main body at rears of the optical fibers for collimating the Stokes beam and the pump beam transmitted from the respective optical fibers;

a diffraction grating installed in the main body at the rear of the collimator lens for diffracting the collimated Stokes beam and the collimated pump beam such that the collimated Stokes beam and the collimated pump beam have the same spectral dispersion;

a reflection mirror installed in the main body for transmitting the reflected Stokes beam and the reflected pump beam, the reflection mirror comprising a dichroic reflection part for transmitting the diffracted pump beam, reflecting the diffracted Stokes beam, and re-reflecting CARS beams generated from the sample to the diffraction grating and a full reflection part for fully reflecting the pump beam transmitted through the dichroic reflection part;

an objective lens installed in the main body at the other side of the main body for condensing the pump beam and the Stokes beam reflected from the reflection mirror to the sample; and a CARS beam transmission part for transmitting the CARS beams to a spectroscope.

2. The spectrally encoded CARS endoscope according to claim 1, wherein the CARS beam transmission part is located at one side of the main body where the optical fibers are installed.

3. The spectrally encoded CARS endoscope according to claim 1, wherein the dichroic reflection part and the full reflection part of the reflection mirror are implemented by a dichroic reflection mirror and a full reflection mirror, respectively, and the spectrally encoded CARS endoscope further comprises an angle adjustment device for adjusting an angle between the dichroic reflection mirror and the full reflection mirror.

4. The spectrally encoded CARS endoscope according to claim 1, wherein the angle adjustment device comprises a support part disposed between the dichroic reflection mirror and the full reflection mirror for supporting the dichroic reflection mirror and adjusting an inclination angle of the dichroic reflection mirror through a movement thereof and a distance adjustment screw coupled to the main body, while the distance adjustment screw is in contact with the support part, for adjusting the movement distance of the support part.

5. The spectrally encoded CARS endoscope according to claim 1, wherein the dichroic reflection part and the full reflection part of the reflection mirror are implemented by a dichroic reflection coating and a full reflection coating formed at one major surface and the other major surface of the reflection mirror, respectively, and the reflection mirror is installed such that the reflection mirror is inclined at a predetermined angle to an incident pump beam and an incident Stokes beam.

6. The spectrally encoded CARS endoscope according to claim 4, wherein the angle of the reflection mirror is decided by an equation below:

$$\alpha = (\theta_{pd} - \theta_{sd})/2n$$

Where, $\alpha$ is an angle of the reflection mirror, $(\theta_{pd} - \theta_{sd})$ is a diffraction angle difference between the pump beam and the Stokes beam, and n is a refractive index of the reflection mirror.

7. The spectrally encoded CARS endoscope according to claim 5, wherein the angle of the reflection mirror is decided by an equation below:

$$\alpha = (\theta pd - \theta sd)/2n$$

Where, $\alpha$ is an angle of the reflection mirror, $(\theta pd - \theta sd)$ is a diffraction angle difference between the pump beam and the Stokes beam, and n is a refractive index of the reflection mirror.

* * * * *